(12) United States Patent
Tang et al.

(10) Patent No.: US 6,448,446 B1
(45) Date of Patent: Sep. 10, 2002

(54) SYNTHESIS OF N,N-DISUBSTITUTED-P-PHENYLENEDIAMINE

(75) Inventors: Li Tang; Yuying Tan, both of San Diego, CA (US)

(73) Assignee: AntiCancer, Inc., San Diego, CA (US)

(*) Notice: Subject to any disclaimer, the term of this patent is extended or adjusted under 35 U.S.C. 154(b) by 0 days.

(21) Appl. No.: 09/760,202

(22) Filed: Jan. 12, 2001

Related U.S. Application Data

(60) Provisional application No. 60/175,742, filed on Jan. 12, 2000.

(51) Int. Cl.[7] .............................................. C07C 209/00
(52) U.S. Cl. ....................... 564/437; 564/416; 564/419; 564/438; 564/394
(58) Field of Search ................................. 564/394, 416, 564/419, 437, 438

(56) References Cited

U.S. PATENT DOCUMENTS 5,985,540 A * 11/1999 Tan et al.
5,998,191 A * 12/1999 Tan et al.
6,066,467 A *  5/2000 Xu et al.

OTHER PUBLICATIONS

Reilly and Hickinbottom, Journal of the Chemical Society (1918) 113:99–111.*

* cited by examiner

*Primary Examiner*—Samuel Barts
(74) *Attorney, Agent, or Firm*—Morrison & Foerster LLP

(57) ABSTRACT

An improved synthesis of N,N,-disubstituted-p-phenylenediamine (DSPDA) preferably di-n-butyl-p-phenylenediamine is disclosed. The improvement rests on the discovery that DSPDA and its salts are extremely sensitive to oxygen so that once the product DSPDA or its salt is formed, oxygen must be excluded from all manipulations.

9 Claims, 1 Drawing Sheet

SYNTHESIS OF N,N-DISUBSTITUTED-P-PHENYLENEDIAMINE

This application claims benefit of Provisional Application Ser. No. 60/475,742 filed Jan. 12, 2000.

TECHNICAL FIELD

The invention relates to an improved synthesis of N,N-disubstituted-p-phenylenediamine, especially the dibutyl form (DBPDA). DBPDA is a useful reagent in colorometric and fluorescence assays.

BACKGROUND ART

U.S. Pat. No. 6,066,467, the contents of which are incorporated by reference, discloses the use of a particular N,N-disubstituted-p-phenylene diamine, DBPDA, in a fluorescence assay for hydrogen sulfide production from the action of homocysteinase. The assay, which is useful to measure homocysteine levels in bodily fluids, shows enhanced sensitivity over similar assays which utilize absorbance by color. Such assays are described in U.S. Pat. Nos. 5,998,191 and 5,985,540, also incorporated by reference. The colorometric reagent counterparts to DBPDA, in addition to this dibutyl derivative, can also be N,N-dipropyl-1, 4-phenylenediamine or the corresponding diethyl or dimethyl derivative.

While the dibutyl derivative, DBPDA, is available commercially, it is not as inexpensive or obtainable in as great quantity as the lower alkyl counterparts. Accordingly, an improved synthesis for DBPDA would be of benefit.

A classic synthesis for this compound is described in Reilly, J. and Hickinbottom, W. J. in *J. Chem.Soc.* (London) (1918) pages 99–111. Two methods are described for the synthesis; of greater relevance to the present invention is the conversion of di-n-butylaniline to the para-nitroso compound with subsequent reduction to the desired product. It has now been found that the described method is unworkable as strictly described, as it is necessary to conduct certain steps of the reaction in an oxygen-free environment. In addition, an improved method for crystallization is described herein. These improvements are applicable to N,N-disubstituted-p-phenylene diamine (DSPDA) generally.

DISCLOSURE OF THE INVENTION

The invention is directed to an improvement over the literature-described synthesis of di-n-butyl-p-phenylenediamine and its salts, as well as DSPDA in general. The improved method, like that described in the prior art, employs the conversions shown in FIG. 1. Both the intermediate nitroso-compound and the phenylenediamine derivative that is the final product can be converted to the acid addition salts using standard techniques. According to the method of the present invention, certain steps in this reaction are conducted in an oxygen-free environment.

Thus, in one aspect, the invention is directed to an improved method to synthesize DSPDA, especially DBPDA, which method comprises treating p-nitroso disubstituted aniline with a reducing agent, and working up the product in the absence of oxygen. In a preferred embodiment, the reducing agent is zinc. Further, the production of the nitroso compound is preferably from treating disubstituted aniline starting material with nitrous acid.

In another aspect, the invention is directed to an improved method to crystallize DSPDA, especially DBPDA, which method comprises treating an absolute ethanol solution of the dihydrochloride with ether.

BEST MODE FOR CARRYING OUT THE INVENTION

Figure 1:
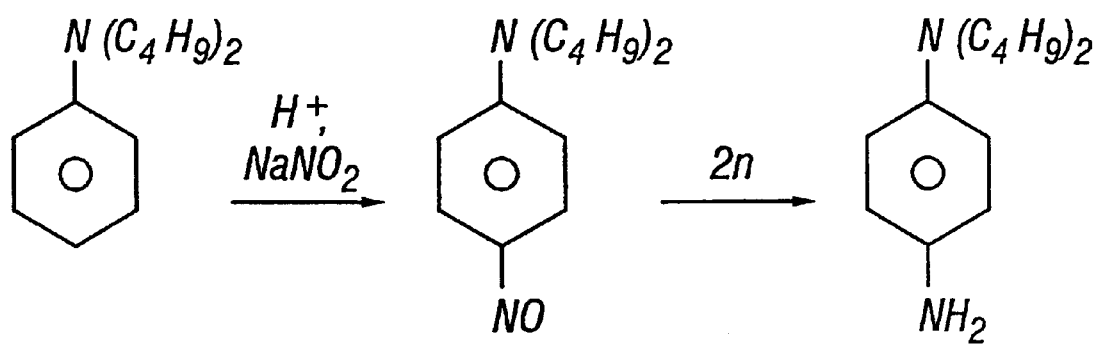
FIG. 1 shows the steps in the conversion of di-n-butylaniline to DBPDA.

In a preferred embodiment, to prepare the nitroso intermediate, an aqueous solution of the starting material, preferably di-n-butylaniline is acidified with concentrated acid, preferably HCl, and then treated with sodium nitrite. The temperature is kept low, preferably at 0° C., and the addition of sodium nitrite to the starting material solution is performed with stirring over 1–2 hours. The crude hydrochloride product precipitates from solution and may, if desired, be re-crystallized.

The recovered di-n-butyl-p-nitrosoaniline hydrochloride prepared is then dissolved in hydrochloric acid and a reducing agent added. A preferred reducing agent is excess zinc dust, although other reducing agents, such as $H_2$ could also be used. When the reduction is complete, the zinc metal is filtered off. It is essential to the method of the invention that the filtrate, from then on, is kept under an atmosphere which excludes oxygen. The filtrate is neutralized with strong base. If zinc is used as a reducing agent, the zinc ion formed initially precipitates and then re-dissolves. During this process, the reaction mixture is kept under nitrogen or other method to exclude oxygen is employed. This also converts the product to the free amine which can then be extracted in a suitable organic solvent, such as ether. These operations, too, must be performed in the absence of oxygen. The non-aqueous layer is then dried and treated with non-aqueous acid to effect precipitation of the salt, preferably the hydrochloride salt of the desired product.

The hydrochloride salt can then be crystallized by dissolving in an alcoholic solvent in the absence of water and in the absence of oxygen and effecting crystallization by addition of ether.

If desired, the DBPDA product can be refluxed in acetone at 70–80° for about two hours.

The resulting DBPDA is useful as a reagent for the colorometric or fluorescence detection of hydrogen sulfide in the presence of a metal ion, such as ferric ion, as described in the above-cited art.

As is known in the art, in addition to DBPDA, other dialkyl substituted phenylene diamines are useful in fluorescence detection of hydrogen sulfide in the presence of a metal ion or other oxidizing agent. Thus, the method described above with particularity for DBPDA is also useful for N,N-disubstituted phenylene diamines in general which also have utility as detection reagents in such assays. Thus, in addition to the di-n-butyl substituted form, the method could be applied to any dialkyl substituted form, as well as forms of the phenylene diamine which have substituents on the ring nitrogen which may themselves be substituted alkyl groups. Thus, for example, also illustrated below is the synthesis of the N,N-disubstituted phenylene diamine wherein the substituents are diethyl aminoethyl substituents.

Thus, in general, the method is useful for preparing analogs where the substituents on the ring nitrogen are the same or different and where they may include alkyl groups which contain one or more heteroatoms such as N or O or which may contain non-interfering substituents such as RO, $R_2N$, wherein R is alkyl (1–4C or H), preferably alkyl 1–4C, or substituted by one or more alkyl groups. The substituents at the ring nitrogen can be any substituents wherein the components of the substituent do not interfere with the overall reaction scheme described herein. In general, the substituents at the ring nitrogen are essentially alkyl (1–10C) with one or two optional heteroatoms selected from O and N, and further substituted by basic or neutral substituents.

In addition, the substituents on the ring nitrogen may include aryl groups which themselves may be optionally substituted; it is preferred that the aryl groups be present in the form of arylalkyl. In the case of some substituents, it may be necessary to protect the substituents during some phases of the preparation procedure. Methods for protection and de-protection of such substituents are well-known in the art.

In addition, while the method of the invention is illustrated using the hydrochloride salt of the DSPDA and hydrochloric acid is used where acidification is required, it is not necessary to use this particular salt. HCl is preferred; however, alternative salts include inorganic salts such as the hydrobromide, the nitrate, or hydrofluoride; salts of organic acids, such as acetates, propionates, glycolates and the like may also be used.

EXAMPLES

The following examples are intended to illustrate but not to limit the invention.

Example 1

Preparation of N,N-Dibutyl-p-Nitrosoaniline Hydrochloride

A solution of N,N-dibutylaniline (10.25 g; 0.05 moles; Aldrich No.: 30,446-8, 97%) in a mixture of concentrated HCl (15 ml; Aldrich No.: 25,814-8, 37%) and distilled water (20 ml) was cooled to −5° C. to −15° C. in a freezing mixture (ice+salt) (Solution A). Sodium nitrite (3.62 g; 0.052 moles; Aldrich No: 43,089-9, granular, 99.5%, DuPont product) was dissolved at room temperature in distilled water (10 ml) and cooled to and kept at 0° C. (Solution B). Cold (0° C.) Solution B was gradually added over 1–2 hours to a magnetically stirred Solution A (at −5 to −15° C.) and the reaction temperature was carefully monitored and not allowed to rise above 0° C. During addition, the reaction mixture changes from pale red to almost black. The mixture was then allowed to attain room temperature over two to three hours. During this time, a dark crystalline mass was deposited. The crystals were collected on Buchner funnel and washed with acetone.

The crystalline mass was dried in vacuum at 40° C. to constant weight. The average yield of the crude product title compound was almost quantitative (10.5 g). The crude product was dissolved in a minimum amount of ethanol (usually around 20 ml absolute ethanol) and pure product precipitated with ether (150–200 ml, 99+%). The yield of the pure product (yellow-greenish crystals) was between 8 and 9 g (80–90% theoretical).

Example 2

Preparation of N,N-Dibutyl-p-Phenylenediamine Dihydrochloride

N,n-dibutyl-p-nitrosoaniline hydrochloride (5 g;0.00196 moles prepared in Example 1 was dissolved in 1:2 HCl (60 ml;0.24M of HCl) (Solution C). Zn dust (5.12 g; 0.0784 moles) was gradually added to the magnetically stirred Solution C placed in a two-neck round-bottom flask (150–250 ml volume) fitted with a reflux condenser. When all the Zn was added, the mixture was heated for an additional hour on a water bath. The reduction was completed when the supernatant was colorless after allowed Zn to settle. Excess zinc dust was collected on a Buchner funnel and washed with warm dilute (4:4) HCl.

The following steps until recovery of the final product as crystals were carried out in the absence of oxygen. Where possible, the steps were performed under an atmosphere of nitrogen; in some cases, when it was impractical to maintain a nitrogen atmosphere (such as extraction into an organic solvent) the operations were conducted rapidly and with minimal exposure to air. The filtrate was treated with excess concentrated NaOH (50% solution in water) under a nitrogen atmosphere until the initially precipitated zinc hydroxide was dissolved. The oily suspended reduction product was extremely sensitive to oxygen and in its presence the product immediately turns from pale to dark blue. If the process is done correctly, excluding oxygen, the product is almost colorless or slightly pale blue.

The whole reaction mixture was then carefully transferred to a separatory funnel, and the basic final product was extracted with several portions of ether (each portion of 50–70 ml), in the absence of oxygen with minimum shaking.

The collected ether layer was dried over anhydrous $K_2CO_3$ overnight, under $N_2$. (The product is also very sensitive to moisture.) Ether solution was filtered off from the drying agent, which was washed with ether (the whole operation should be done as quickly as possible) and the filtrate was treated with an excess of anhydrous HCl in ether (50–70 ml, 1.0 M, solution in diethyl ether. Ethanol (20–40 ml) was also added to promote crystallization. The product crystals were collected with a Buchner funnel and dried as soon as possible under $N_2$.

If the just-described operations are done strictly excluding oxygen and moisture, the obtained product is an almost colorless crystalline substance, and the yield is 3.5–4 g.

To recrystallize the product, the crude DBPDA HCl was dissolved in a minimum of ethanol and ether was added to crystallize.

Example 3

Synthesis of 4-amino-N,N-bis[2-(N',N'-diethylamino)ethylaniline

A. Preparation of 4-nitro-N,N-bis[2-(N',N'-diethylamino)ethyl]aniline: 1-fluoro-4-nitrobenzene in is dissolved in N,N-dimethylformamide (DMF) in a 100 ml flask. The solution is stirred magnetically, and then N,N,N'N'-tetraethyldiethylenetriamine is added to the solution. The mixture is heated for 2 h at 110° C., and then cooled to room temperature. The product is extracted with hexane and purified on a silica gel column.

B. Preparation of 4-amino-N,N-bis[2-(N',N'-diethylamino)ethyl]aniline: The 4-nitro-N,N-bis[2-(N',N'-diethylamino)ethyl]aniline from paragraph A is dissolved in 1:2 HCl in 200 ml in a two-neck flask. The solution is refluxed with stirring. Zn is added to the solution slowly, and the mixture is kept boiling until the solution becomes colorless. A solution of 50% NaOH is added under $N_2$ until the white precipitate dissolves. The product is extracted with ether and crystallized HCl/ether under $N_2$.

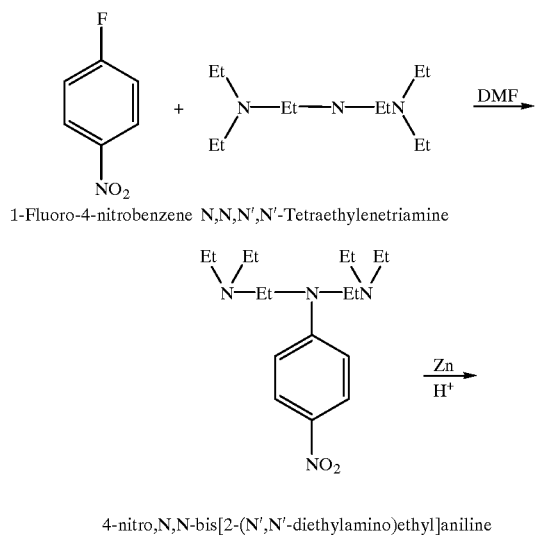

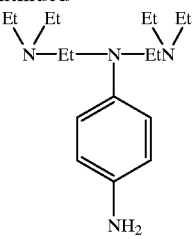

4-amino,N,N-bis[2-(N',N'-diethylamino)ethyl]aniline

What is claimed is:

1. In a method to obtain N,N,-disubstituted-p-phenylene-diamine (DSPDA) from an acidic reaction mixture containing a DSPDA acid addition salt, which method comprises neutralizing said acidic reaction mixture with base, the improvement which comprises conducting said neutralizing with base under conditions which exclude oxygen.

2. A method to obtain DSPDA from DSPDA-acid addition salt which method comprises treating an acidic solution of said acid addition salt with base under conditions which exclude oxygen.

3. The method of claim 2 which further includes extracting the free DSPDA into an organic solvent under conditions where oxygen is excluded.

4. The method of claim 3 wherein the organic solvent is ether.

5. The method of claim 2 which further includes precipitating DSPDA acid addition salt from said organic solvent by adding anhydrous acid under conditions that exclude oxygen.

6. A method to crystallize DSPDA-acid addition salt which method comprises dissolving said DBPDA-acid addition salt in ethanol and adding ether to effect crystallization.

7. The method of any of claims 1–6 wherein the DSPDA is a dialkyl PDA.

8. The method of claim 7 wherein the dialkyl PDA is di-n-butyl PDA (DBPDA).

9. The method of any of claims 1–6 wherein the acid addition salt is the hydrochloride and/or the acidic reaction mixture or acidic solution is derived from HCl.

* * * * *